(12) United States Patent
Tanaka et al.

(10) Patent No.: US 8,703,412 B2
(45) Date of Patent: Apr. 22, 2014

(54) METHOD OF MEASURING LIPOARABINOMANNAN AND APPLICATION THEREOF

(75) Inventors: Shigenori Tanaka, Kodaira (JP); Shoji Takahashi, Higashiyamato (JP)

(73) Assignee: Seikagaku Corporation, Tokyo (JP)

( * ) Notice: Subject to any disclaimer, the term of this patent is extended or adjusted under 35 U.S.C. 154(b) by 593 days.

(21) Appl. No.: 12/905,685

(22) Filed: Oct. 15, 2010

(65) Prior Publication Data

US 2011/0033939 A1     Feb. 10, 2011

Related U.S. Application Data

(62) Division of application No. 10/584,071, filed as application No. PCT/JP2004/019206 on Dec. 22, 2004, now Pat. No. 7,851,179.

(30) Foreign Application Priority Data

Dec. 22, 2003 (JP) .................................. 2003-425472

(51) Int. Cl.
- C12Q 1/04 (2006.01)
- C12Q 1/06 (2006.01)
- C12Q 1/08 (2006.01)
- G01N 33/92 (2006.01)

(52) U.S. Cl.
USPC ............................................... 435/4; 435/34

(58) Field of Classification Search
USPC ........................................ 435/4, 34; 436/71.1
See application file for complete search history.

(56) References Cited

U.S. PATENT DOCUMENTS

| | | | |
|---|---|---|---|
| 4,495,294 | A | 1/1985 | Nakahara et al. |
| 5,652,332 | A | 7/1997 | Little, II |
| 5,681,710 | A | 10/1997 | Tanaka et al. |
| 7,638,340 | B2 * | 12/2009 | Tanaka et al. ............. 436/71 |

FOREIGN PATENT DOCUMENTS

| | | |
|---|---|---|
| EP | 0569033 A2 | 11/1993 |
| JP | 58-085162 A | 5/1983 |
| JP | 6-70796 A | 3/1994 |
| JP | 6-273421 A | 9/1994 |
| JP | 8-122334 A | 5/1996 |
| WO | 90/02951 A1 | 3/1990 |
| WO | 97/34149 A1 | 9/1997 |
| WO | 98/34119 A1 | 8/1998 |

OTHER PUBLICATIONS

Raetz et al., 2002. Lipopolysaccharide Endotoxins. Annual Review of Biochemistry, vol. 71, pp. 635-700.*
Adams et al. 1993. Regulation of Murine Macrophage Effector Functions by Lipoarabinomannan from Mycobacterial Strains with Different Degrees of Virulence. Infection and Immunity, vol. 61, pp. 4173-4181.*
Juffermans et al. 2000, Mycobacterial Lipoarabinomannan Induces an Inflammatory Response in the Mouse Lung: A Role for Interleukin-1. American Journal Respir. Crit. Care Med., vol. 162, pp. 486-489.*
Japanese Office Action issued in Application No. 2005-516506; dated Oct. A, 2010.
A Molloy, et al., Suppression of T-cell proliferation by *Mycobacterium leprae* and its products: The role of lipopolysaccharicle. Proc.Natl.Acad.Sci.USA, 1990, pp. 973-977, vol. 67.
Butt, K. I., et al., "Immunopathological Strain of Lipoarabinomannan-B (LAM-B) for Diagnosis of Leprosy", Jpn. J. Lepr., 1993, vol. 62, No. 1, p. 13-20.
Delams, Carole et al., "Comparitive structural study of the mannosylated-lipoarabinomannans from *Mycobacterium bovis* BCG vaccine strains: characterization and localization of succinates", Glycobiology, 1997, vol. 7, No. 6, p. 811-817.
Hamasur, Beston, et al., "Rapid diagnosis of tuberculosis by detection of mycobacterial lipoarabinomannan in urine", Journal of Microbiological Methods, 2001, vol. 45, No. 1, p. 41-52.
Savedra., R., Jr., et al., *Mycobacterial lipoarabinomannan* recognition requires a receptor that shares components of the endotoxin signaling system, J Immunol., Sep. 1996, pp. 2549-2554, vol. 157, No. 6.
Tan, N.S., et al., Definition of endotoxin binding sites in horseshoe crab Factor C recombinant sushi proteins and neutralization of endotoxin by sushi peptides. FASEB J., Sep. 2000, pp. 1801-1813, vol. 14.
Tessema,, T. A., et al., Diagnostic evaluation of urinary lipoarabinomannan at an Ethiopian tuberculosis centre, Scand J Infect Dis., 2001, pp. 279-284, vol. 33, No. 4.
Zhang et al., "Mechanism of Stimulation of Interleukin-1beta and Tumor Necrosis Factor-alpha by *Mycobacterium tuberculosis* Components" Journal of Clinical Investigation, New York, vol. 91, No. 5, May 1993, pp. 2076-2083.
International Search Report for PCT/JP04/019206 dated Feb. 8, 2005.
Japanese Office Action issued on Jul. 27, 2010 in corresponding Japanese Patent Application No. 2005-516508.
Notification of Reasons for Refusal issued in counterpart Japanese Application No. 2005-516508, dated Feb. 9, 2010.
Supplementary European Search Report for EP 04 80 7563 dated Oct. 12, 2007.

* cited by examiner

*Primary Examiner* — Jon P Weber
*Assistant Examiner* — Kailash C Srivastava
(74) *Attorney, Agent, or Firm* — Sughrue Mion, PLLC

(57) ABSTRACT

A method for measuring LAM and a method for detecting an acid-fast bacterium, which comprise at least a step of allowing a *Limulus* reagent to contact with a LAM-containing sample; a method for removing reactivity of LAM with a *Limulus* reagent, which comprises at least a step of allowing a predetermined substance to coexist with a LAM-containing sample; a method for measuring Et in a LAM-containing sample and a method for detecting an Et-related disease, which each is a method for measuring an endotoxin using a *Limulus* reagent, which comprises at least a step of removing reactivity of LAM with a *Limulus* reagent by the above-described removing method; a method for measuring BG in a LAM-containing sample and a method for detecting mycosis, which is a method for measuring BG using a *Limulus* reagent, which comprises at least a step of removing reactivity of LAM with a *Limulus* reagent by the described-described removing method; and the like.

1 Claim, No Drawings

METHOD OF MEASURING LIPOARABINOMANNAN AND APPLICATION THEREOF

CROSS-REFERENCE TO RELATED APPLICATION

This is a divisional of application Ser. No. 10/584,071 filed Jun. 22, 2006 (now U.S. Pat. No. 7,851,179 B2 issued Dec. 14, 2010), which is a National Stage of PCT/JP2004/019206 filed Dec. 22, 2004 which claims priority from Japanese Application No. 2003-425472 filed Dec. 22, 2003, the disclosures of which are incorporated by reference herein.

TECHNICAL FIELD

The present invention relates to a method for measuring lipoarabinomannan, a kit to be used therein, a method for removing reactivity of lipoarabinomannan with a *Limulus* reagent, a method for measuring endotoxin and $(1{\rightarrow}3)$-$\beta$-glucan using the same, a kit for use therein, an agent for binding of lipoarabinomannan and the like.

BACKGROUND ART

A *Limulus* reagent (also called a lysate reagent) is a reagent which comprises a horseshoe crab amoebocyte lysate as the main component and is used for the detection and measurement of an endotoxin (hereinafter referred to as "Et") and a $(1{\rightarrow}3)$-$\beta$-glucan (hereinafter referred to as "BG"). Since Et and BG have reactivity with a *Limulus* reagent, when the *Limulus* reagent and there substances contact with one another, a cascade reaction in which various factors in the *Limulus* reagent are concerned (hereinafter referred to as "*Limulus* reaction") is induced, so that these substances can be detected and measured by detecting this reaction.

On the other hand, it is known that a lipoarabinomannan (hereinafter referred to as "LAM") is a cell wall component specific to acid-fast bacteria (e.g., tubercle bacillus, etc.).

Patent Reference 1 discloses a *Limulus* reaction-activating substance which is physically different from Et and BG, an inactivation method thereof, a measuring method thereof and the like. However, this substance is completely different from LAM as is described later, and there is no disclosure or suggestion that LAM has reactivity with a *Limulus* reagent.
Patent Reference 1: JP-A-10-185924

DISCLOSURE OF THE INVENTION

Problems to be Solved by the Invention

An object of the present invention is to provide a method for measuring LAM, a kit to be used therein, a method for removing reactivity of LAM with *Limulus* reagent, a method for measuring Et and BG using the same, a kit for use therein, an agent for binding of LAM and the like.

Means for Solving the Problems

The present inventors have conducted intensive studies in order to solve the above-described problems and found as a result for the first time that LAM has reactivity with a *Limulus* reagent and, based on this finding, have provided a method for measuring LAM, a kit to be used therein, a method for removing reactivity of LAM with *Limulus* reagent, a method for measuring Et and BG using the same, a kit for use therein and the like.

That is, the present invention provides a method for measuring LAM in a sample, which comprises at least a step of allowing a *Limulus* reagent to contact with a "LAM-containing sample" (hereinafter referred to as "LAM-measuring method of the present invention"). It is preferable that this method further comprises a step of heating the "LAM-containing sample" before the contact with the *Limulus* reagent. In addition, it is preferable that the *Limulus* reagent is an Et-specific *Limulus* reagent.

Also, the present invention provides a method for detecting an acid-fast bacterium, which comprises using the LAM-measuring method of the present invention (hereinafter referred to as "acid-fast bacterium-detecting method of the present invention"). It is preferable that the acid-fast bacterium to be detected is a tubercle bacillus.

Also, the present invention provides a kit for measuring LAM, which comprises a *Limulus* reagent as a component (hereinafter referred to as "LAM-measuring kit of the present invention"). It is preferable that the *Limulus* reagent is an Et-specific *Limulus* reagent.

Also, the present invention provides a kit for detecting an acid-fast bacterium, which comprises the LAM-measuring kit of the present invention (hereinafter referred to as "acid-fast bacterium detection kit of the present invention"). It is preferable that the acid-fast bacterium to be detected is a tubercle bacillus.

Also, the present invention provides a method for removing reactivity of LAM in a "LAM-containing sample" with a *Limulus* reagent, which comprises at least a step of allowing one or more substance(s) selected from the following group to coexist with the sample (hereinafter referred to as "reactivity-removing method of the present invention"):
a surfactant, an anti-tuberculosis antibody, an anti-LAM antibody, BG, a carboxymethylated BG, a factor G activation inhibitor, a strong alkaline substance, polymyxin B, colistin, concanavalin A, histidine and histamine.

Also, the present invention provides a method for measuring Et in a "LAM-containing sample", which is a method for measuring Et using a *Limulus* reagent, which comprises at least a step of removing reactivity of LAM with a *Limulus* reagent by the reactivity-removing method of the present invention (hereinafter referred to as "Et-measuring method of the present invention"). It is preferable that the *Limulus* reagent is an Et-specific *Limulus* reagent.

Also, the present invention provides a method for detecting an Et-related disease, which comprises using the Et-measuring method of the present invention (hereinafter referred to as "Et-related disease detection method of the present invention").

Also, the present invention provides a kit for measuring Et, which comprises a *Limulus* reagent and one or more substance(s) selected from the following group as components (hereinafter referred to as "Et-measuring kit of the present invention"):
a surfactant, an anti-tuberculosis antibody, an anti-LAM antibody, BG, a carboxymethylated BG, a factor G activation inhibitor and a strong alkaline substance.

It is preferable that the *Limulus* reagent is an Et-specific *Limulus* reagent.

Also, the present invention provides a kit for detecting an Et-related disease, which comprises the Et-measuring kit of the present invention (hereinafter referred to as "Et-related disease detection of the present invention").

Also, the present invention provides a method for measuring BG using a *Limulus* reagent in a "LAM-containing sample", which comprises at least a step of removing reactivity of LAM with a *Limulus* reagent by the reactivity-removing method of the present invention (hereinafter referred to as "BG-measuring method of the present invention"). It is preferable that the *Limulus* reagent is a BG-specific *Limulus* reagent.

Also, the present invention provides a method for detecting mycosis, which comprises using the BG-measuring method of the present invention (hereinafter referred to as "mycosis detection method of the present invention").

Also, the present invention provides a kit for measuring BG, which comprises a *Limulus* reagent and one or more substance(s) selected from the following group as components (hereinafter referred to as "BG-measuring kit of the present invention"):

a surfactant, an anti-tuberculosis antibody, an anti-LAM antibody, a strong alkaline substance, polymyxin B, colistin, concanavalin A, histidine and histamine.

Also, the present invention provides a kit for detecting mycosis, which comprises the BG-measuring kit of the present invention (hereinafter referred to as "mycosis detection kit of the present invention").

Also, the present invention provides an agent for binding of LAM, which comprises one or more substance(s) selected from the following group as an active ingredient (hereinafter referred to as "binder of the present invention"):

an anti-tuberculosis antibody, an anti-LAM antibody, (1→3)-β-glucan, a carboxymethylated (1→3)-β-glucan, a factor G activation inhibitor, polymyxin B, colistin, concanavalin A, histidine and histamine.

Effect of the Invention

The LAM-measuring method of the present invention, the acid-fast bacterium detection method of the present invention, the LAM-measuring kit of the present invention and the acid-fast bacterium detection kit of the present invention can be used for measuring and detecting LAM and acid-fast bacteria conveniently, quickly and inexpensively and therefore are markedly useful.

In addition, the reactivity-removing method of the present invention can be used for removing influence of LAM in the *Limulus* reaction conveniently, quickly and inexpensively and therefore is markedly useful.

The Et-measuring method of the present invention, the Et-related disease detection method of the present invention, the Et-measuring kit of the present invention and the Et-related disease detection kit of the present invention can be used for measuring and detecting Et and Et-related diseases specifically and also conveniently, quickly and inexpensively and therefore are markedly useful.

The BG-measuring method of the present invention, the mycosis detection method of the present invention, the BG-measuring kit of the present invention and the mycosis detection kit of the present invention can be used for measuring and detecting BG and mycosis specifically and also conveniently, quickly and inexpensively and therefore are markedly useful.

The agent for binding of the present invention can be used for detecting and measuring LAM and for removing LAM and therefore is markedly useful.

BEST MODE FOR CARRYING OUT THE INVENTION

<1> LAM-Measuring Method of the Present Invention

The LAM-measuring method of the present invention is a method for measuring LAM in a sample, which comprises at least a step of allowing a *Limulus* reagent to contact with "the LAM-containing sample".

The "*Limulus* reagent" is not particularly limited, so long as it is a reagent which comprises a horseshoe crab amoebocyte lysate as the main component. The kind of this horseshoe crab is also not limited, and the amoebocyte lysate of any one of *Limulus polyphemus* (North American horseshoe crab) and *Tachypleus tridentatus*, *Tachypleus gigas* and *Tachypleus rotundicauda* (Asian horseshoe crab) can be used. The amoebocyte lysate can be produced by a conventionally known method. In addition, a *Limulus* reagent which is on the market may be used.

This *Limulus* reagent may be a *Limulus* reagent prepared in such a manner that it does not react with BG (referred to as "Et-specific *Limulus* reagent" in this specification) or a *Limulus* reagent which reacts with Et and BG, but it is preferably an "Et-specific *Limulus* reagent". This Et-specific *Limulus* reagent can be produced by a conventionally known method, or a commercially available product may be used.

The "LAM-containing sample" is not particularly limited, so long as it is a sample that contains LAM or has a possibility of containing LAM. Since LAM is a cell wall component specific to acid-fast bacteria, living cells or dead cells themselves of an acid-fast bacterium (e.g., tubercle bacillus, etc.), cell walls thereof, a sample containing the cell wall component or having a possibility of containing the same can be exemplified. Examples of such a sample include tubercle bacillus vaccine and the like.

In addition, a "sample derived from the living body" can also be used as the "LAM-containing sample". The "sample derived from the living body" is not particularly limited too, but a body fluid is preferable. The body fluid is not particularly limited, so long as it is a body fluid that contains LAM or has a possibility of containing the same. Examples include blood (in this specification, this is used as a general idea including serum and plasma), urine, sweat, saliva, tears, synovial fluid, expectoration, milk, spinal fluid and the like. Among these, blood is preferable.

In this connection, when blood is used as the "sample derived from the living body", it is preferable to remove or inactivate *Limulus* reaction-interfering factors in blood (serine protease, serine protease inhibitor, etc.) in advance by a conventionally known method (e.g., the method described in JP-A-58-85162, etc.).

In addition, the method for "contacting" a *Limulus* reagent with a sample is also not limited, so long as a factor in the *Limulus* reagent is allowed to contact with a LAM molecule in the sample, so that the sample may be added to the *Limulus* reagent, the *Limulus* reagent may be added to the sample, or both may be added at the same time.

The LAM-measuring method of the present invention may contain another step, so long as it contains the step of allowing a *Limulus* reagent and a "LAM-containing sample" to contact with each other. For example, it is preferable that it further comprises a step of heating the "LAM-containing sample" before its contact with the *Limulus* reagent. According to the specification, the "heating" means that a substance under room temperature is heated. The temperature after heating is not particularly limited, but the heating is preferably carried out at from 37 to 121° C., preferably from 60 to 100° C., particularly 95° C. The period of time for keeping the heated state is not particularly limited too, but it is preferable to keep the heated state for from 5 to 60 minutes, preferably from 10 to 30 minutes, and particularly about 20 minutes.

When a *Limulus* reagent is contacted with a sample, LAM in the sample activates the factor C (known as a factor which is activated by Et) in the *Limulus* reagent, and a *Limulus* reaction is induced thereby.

By detecting and measuring this *Limulus* reaction, LAM in the sample can be measured. The *Limulus* reaction can be detected and measured by conventionally known methods. For example, chromogenic assay (endpoint assay or kinetic assay), gel-clot assay, turbidimetric assay (endpoint assay or kinetic assay) and the like conventionally known methods can be employed as the detecting and measuring methods corresponding to respective methods.

In this connection, the "measurement" as used herein is a general idea which includes not only quantitative measurement but also qualitative measurement (measurement in the presence or absence of LAM, etc.).

As the quantitative measurement of LAM, various methods can be employed in response to the object. For example, strict determination can be carried out by preparing a calibration curve or a relational expression on the relationship between the LAM concentration and the strength of *Limulus* reaction using a sample having already known LAM concentration and using this. In addition, when strict determination is not necessary, amounts of LAM between samples may be compared using two or more samples. Since LAM induces a *Limulus* reaction, the amount of LAM in a sample is large when strength of the *Limulus* reaction is high.

LAM can be qualitatively measured by detecting the presence or absence of the *Limulus* reaction. Since LAM induces a *Limulus* reaction, LAM is present in a sample when the *Limulus* reaction is detected.

<2> Acid-Fast Bacteria Detection Method of the Present Invention

The acid-fast bacteria detection method of the present invention is a method for detecting an acid-fast bacterium, which comprises using the LAM-measuring method of the present invention.

The acid-fast bacteria detection method of the present invention is a method in which the LAM-measuring method of the present invention is directly applied to the detection of acid-fast bacteria. Since LAM is a cell wall component specific to acid-fast bacteria, detection of an acid-fast bacterium can be carried out by measuring LAM.

The LAM-measuring method of the present invention should be referred to as the above-described <1>. According to the acid-fast bacteria detection method of the present invention, a sample containing an acid-fast bacterium or having a possibility of containing an acid-fast bacterium is used as the "LAM-containing sample" of the LAM-measuring method of the present invention.

The bacteria to be detected are not particularly limited, so long as they are bacteria classified as acid-fast bacteria. Examples include bacteria belonging to the genus *Mycobacterium*, the genus *Nocardia*, the genus *Rhodococcus*, the genus *Gordonia*, the genus *Corynebacterium* and the like. Among these, a tubercle bacterium (belonging to the genus *Mycobacterium*) is preferable.

In addition, the acid-fast bacterium to be detected may be a living cell or dead cell.

Acid-fast bacteria in such a sample can be detected by using the LAM-measuring method of the present invention.

In this connection, the "detection" of acid-fast bacteria as used herein is a general idea which includes not only a qualitative detection (detection of the presence or absence of acid-fast bacteria) but also a quantitative detection (detection of the amount of acid-fast bacteria, detection of the malignancy of acid-fast bacteria infection, etc.).

The acid-fast bacteria can be qualitatively measured by detecting the presence or absence of a *Limulus* reaction. Since LAM as a cell wall component specific to acid-fast bacteria induces a *Limulus* reaction, an acid-fast bacterium is present in the sample when the *Limulus* reaction is detected.

As the quantitative measurement of an acid-fast bacterium, various methods can be employed in response to the object. For example, strict determination can be carried out by preparing a calibration curve or a relational expression on the relationship between the amount of the acid-fast bacterium and the strength of *Limulus* reaction using a sample having already known acid-fast bacterium amount and using this. In addition, when strict determination is not necessary, amount of the acid-fast bacterium between samples may be compared using two or more samples. Since LAM which is a cell wall component specific for acid-fast bacteria induces a *Limulus* reaction, amount of the acid-fast bacterium in a sample is large when strength of the *Limulus* reaction is high.

<3> LAM-Measuring Kit of the Present Invention

The LAM-measuring kit of the present invention is a kit for measuring LAM, which comprises a *Limulus* reagent as a component. Explanation for "*Limulus* reagent" is the same as in the above-described <1>. That is, it is preferable that this *Limulus* reagent is also an Et-specific *Limulus* reagent.

The LAM-measuring kit of the present invention may further contain another component, so long as it comprises at least a "*Limulus* reagent" as a component. For example, distilled water for blank test use, a reaction reagent solution, a buffer for reaction use and the like can be cited as such a component. In addition, the LAM-measuring kit of the present invention can also contain a positive control (QC control) or the like for the purpose of keeping the practice level between measuring batches at a certain level.

These components can be preserved by containing in respectively separate containers.

LAM using the LAM-measuring kit of the present invention can be measured in accordance with the LAM-measuring method of the present invention described in the above-described <1>.

<4> Acid-Fast Bacteria Detection Kit of the Present Invention

The acid-fast bacteria detection kit of the present invention is a kit for detecting an acid-fast bacterium, which comprises the LAM-measuring kit of the present invention. Explanation for the LAM-measuring kit of the present invention should be referred to the above-described <3>.

Explanation for the acid-fast bacteria to be detected by acid-fast bacteria detection kit of the present invention is the same as in the above-described acid-fast bacteria detection method of the present invention of the above-described <2>. That is, it is preferable that the acid-fast bacterium to be detected is a tubercle bacillus.

Acid-fast bacteria using the acid-fast bacteria detection kit of the present invention can be detected in accordance with the acid-fast bacteria detection method of the present invention of the above-described <2>.

<5> Reactivity Removal Method of the Present Invention

The reactivity-removing method of the present invention is a method for removing reactivity of LAM in a "LAM-containing sample" with a *Limulus* reagent, comprising at least a step of allowing one or more substance(s) selected from the following group to coexist with the sample:

a surfactant, an anti-tuberculosis antibody, an anti-LAM antibody, BG, a carboxymethylated BG, a factor G activation inhibitor, a strong alkaline substance, polymyxin B, colistin, concanavalin A, histidine and histamine.

Explanation for the "LAM-containing sample" and "*Limulus* reagent" are the same as in the LAM-measuring method of the present invention of the above-described <1>.

The "surfactant" which can be used herein is not particularly limited, so long as it does not spoil the reactivity of Et and BG with the *Limulus* reagent, and it does not exert inhibitory action upon various factors which are present in the *Limulus* reagent and concerned in the *Limulus* reaction. For example, it may be any one of a cationic surfactant, an anionic surfactant, an amphoteric surfactant, a nonionic surfactant, a natural surfactant and the like.

Among these, it is preferable to select a nonionic surfactant which has less direct action upon Et. In this connection, these surfactants may be used by optionally combining them.

Among nonionic surfactants, a surfactant having a structure in which its hydrophilic moiety has a polyoxyethylene (hereinafter also referred to as "polyoxyethylenes") is preferable. As the polyoxyethylenes, a polyoxyethylene alkyl ether (represented by a formula $C_nN_{2n+1}(OCH_2CH_2)_xOH$, and generally abbreviated and described as $C_nE_x$), a polyoxyethylene alkyl phenyl ether in which a phenyl group is inserted between an alkyl chain and a polyoxyethylene chain ($C_n\Phi E_x$) and an acyl polyoxyethylene sorbitan ($C_n$sorbitan$E_x$) and the like can be cited, and these are called by general names (trade names) of Brij ($C_nE_x$), Tergitol ($C_nE_x$), Triton X ($C_n\Phi E_x$) and Tween ($C_n$sorbitan$E_x$), respectively, and generally used for many purposes such as solubilization of membrane proteins.

The polyoxyethylene chain (the "$(OCH_2CH_2)_xOH$" moiety in the above-described formula, also referred to as "Ex") of the polyoxyethylenes which can be used herein is not particularly limited, but a compound has preferably an integer of x=2 to 25, more preferably an integer of x=4 to 23, and most preferably an integer of x=7 to 13. In addition, the number of carbon atoms of the alkyl group (the "$C_nH_{2n+1}$" moiety described above, also referred to as "Cn") of the polyoxyethylenes which are used herein is not particularly limited, but a compound having an integer of n=8 to 18 is preferable.

Examples of such polyoxyethylenes include polyoxyethylene dodecyl ether, polyoxyethylene hexadecyl ether (also called polyoxyethylene cetyl ether), polyoxyethylene isooctyl phenyl ether, polyoxyethylene nonyl phenyl ether, polyoxyethylene fatty acid ester, polyoxyethylene sorbitol ester and the like. Among these, polyoxyethylene hexadecyl ether is markedly preferable. In addition, it is preferable that these surfactants are used as aqueous solutions and have a certain micelle size.

In this connection, the solvent of these aqueous surfactant solutions may be a buffer. The buffer is preferably a buffer adjusted to a pH value of approximately from 7 to 9, and examples include Good's buffer [e.g., HEPES (N-2-hydroxyethyl-piperazine-N'-2-ethanesulfonic acid buffer), cholamine chloride buffer, BES buffer, MOPS buffer, TES buffer, HEPPS buffer (N-2-hydroxyethyl-piperazine-N'-3-propanesulfonic acid), Tricine buffer, glycinamide buffer, Bicine buffer, TAPS buffer or the like], Tris-HCl buffer and the like.

An amount of the surfactant to be coexisted with the "LAM-containing sample" can be optionally changed according to the kind and the like of the surfactant and therefore is not particularly limited. As specific concentration of the surfactant, generally from 0.001% to 0.8% (w/v), preferably from 0.003% to 0.5% (w/v), more preferably from 0.005% to 0.3% (w/v) and the like, as the final concentration when contacted with the "LAM-containing sample", can be exemplified.

Also, the "anti-tuberculosis antibody" which can be used herein is not particularly limited, so long as it is an antibody which binds to the LAM existing in the cell wall of a tubercle bacillus, and it may be produced by a conventionally known method using a tubercle bacillus, a cell wall component thereof or the like as the antigen, or may be commercially available. Among these, an antibody which specifically binds to the LAM existing in the cell wall of a tubercle bacillus is preferable.

In addition, the "anti-LAM antibody" which can be used herein is not particularly limited, so long as it is an antibody which binds to LAM, and it may be produced by a conventionally known method using LAM as the antigen, or may be commercially available. Among these, an antibody which specifically binds to LAM is preferable.

These antibodies may be not only those which completely maintain the molecular structure of immunoglobulin as a matter of course, but also those which are made into fragments containing Fab by treating with a protease (e.g., plasmin, pepsin, papain, etc.) that does not degrade the antigen-binding site (Fab). Examples of the fragment containing Fab of antibody include Fabc, (Fab')$_2$ and the like, in addition to Fab.

In addition, when nucleotide sequences of the genes encoding these antibodies or amino acid sequences of these antibodies are determined, Fab-containing fragments of these antibodies or chimeric antibodies thereof can also be prepared by genetic engineering techniques. Such Fab-containing fragments of these antibodies or chimeric antibodies thereof are also included in the general idea of "antibody" according to this specification.

Amounts of these antibodies to be coexisted with the "LAM-containing sample" can be optionally changed according to the kind and the like of each antibody and therefore are not particularly limited.

Also, the "BG" which can be used herein is also not particularly limited, and examples include but pachyman, curdlan, CSBG (BG derived from *Candida albicans* cells) and the like. Among these, pachyman is preferable. In addition, the BG may not only contain β-1,3 bond alone but also have a branch through β-1,6 bond or the like.

In addition, the BG may be a derivative in which a functional group or the like is modified. Examples of the derivative include carboxymethylated BG. Particularly, carboxymethylcurdlan is preferable.

Amounts of the BG and a derivative thereof to be coexisted with the "LAM-containing sample" can be optionally changed in response to their kinds, molecular sizes and the like and therefore are not particularly limited.

In addition, the "factor G activation inhibitor" which can be used herein is not particularly limited too, so long as it is a substance having the action to inhibit activation of the factor G which is present in the *Limulus* reagent, and examples include the polyglucoside and the like described in WO 90/02951. An amount of the "factor G activation inhibitor" to be coexisted with the "LAM-containing sample" can be optionally changed according to the kind and the like of the "factor G activation inhibitor" and therefore is not particularly limited.

In addition, the "strong alkaline substance" which can be used herein is not particularly limited too, but an alkali metal hydroxide is preferable. The alkali metal hydroxide includes sodium hydroxide, potassium hydroxide and the like.

Also, as the "polymyxin B", "colistin", "concanavalin A", "histidine" and "histamine" which can be used herein, those which are on the market can also be used.

The order, method and the like in allowing these substances to coexist with the "LAM-containing sample" are not particularly limited, so long as these substances can be present in the "LAM-containing sample" without causing their modification or destruction.

The method for allowing these substances to coexist with the "LAM-containing sample" is attained in general by thoroughly mixing the "LAM-containing sample" with these substances. Also, regarding the order of allowing these substances to coexist with the "LAM-containing sample", these substances may be added to the *Limulus* reagent, and their mixing and reaction with the "LAM-containing sample" may be carried out at the same time, but it is preferable from the viewpoint of the effect that they are mixed with the "LAM-containing sample" in advance prior to the contact of the *Limulus* reagent with the "LAM-containing sample".

By the reactivity-removing method of the present invention, reactivity of the LAM in the "LAM-containing sample" with the *Limulus* reagent can be specifically removed.

<6> Et-Measuring Method of the Present Invention

The Et-measuring method of the present invention is a method for measuring Et using a *Limulus* reagent in a "LAM-containing sample", which comprises at least a step of removing reactivity of LAM with a *Limulus* reagent by the reactivity-removing method of the present invention.

Explanations for the "*Limulus* reagent" and the "LAM-containing sample" are the same as in the above-described <1> LAM-measuring method of the present invention. That is, it is preferable that this *Limulus* reagent is also an Et-specific *Limulus* reagent.

Also, the reactivity-removing method of the present invention should be referred to the above-described <5>. However, it is necessary to use a substance other than polymyxin B, colistin, concanavalin A, histidine and histamine in this case.

The Et-measuring method of the present invention may contain other steps, so long as it is a method for measuring Et using a *Limulus* reagent, wherein it comprises a step of removing reactivity of LAM with a *Limulus* reagent by the reactivity-removing method of the present invention.

In addition, the timing for removing reactivity of LAM with a *Limulus* reagent by the reactivity-removing method of the present invention is also not limited, but it is preferable to arrange the step of removing reactivity of LAM with a *Limulus* reagent by the reactivity-removing method of the present invention before the contact of the *Limulus* reagent with the "LAM-containing sample". Explanation for the "contact" as used herein is the same as in the above-described <1> LAM-measuring method of the present invention.

According to the Et-measuring method of the present invention, the reactivity of LAM in the "LAM-containing sample" with a *Limulus* reagent is removed, so that Et in the sample can be measured without influence of LAM.

The *Limulus* reaction induced by Et can be detected or measured by a conventionally known method. For example, conventionally known methods, such as chromogenic assay (endpoint assay or kinetic assay), gel-clot assay and turbidimetric assay (endpoint assay or kinetic assay), can be employed as the detecting and measuring methods corresponding to respective methods.

As described above, the "measurement" as used in this specification is a general idea which includes not only quantitative measurement but also qualitative measurement (measurement of the presence or absence of Et, etc.).

As the quantitative measurement of Et, various methods can be employed in response to the object. For example, strict determination can be carried out by preparing a calibration curve or a relational expression on the relationship between the Et concentration and the strength of *Limulus* reaction using a sample having already known Et concentration and using this. In addition, when strict determination is not necessary, amounts of Et between samples may be compared using two or more samples. Since Et induces a *Limulus* reaction, the amount of Et in a sample is large when strength of the *Limulus* reaction is high.

Et can be qualitatively measured by detecting the presence or absence of the *Limulus* reaction. Since Et induces a *Limulus* reaction, Et is present in a sample when the *Limulus* reaction is detected.

<7> Et-Related Disease Detection Method of the Present Invention

The Et-related disease detection method of the present invention is a method for detecting an Et-related disease, which comprises using the Et-measuring method of the present invention.

The Et-related disease detection method of the present invention is a method in which the Et-measuring method of the present invention is directly applied to the detection of Et-related diseases.

The Et-measuring method of the present invention should be referred to as the above-described <6>. According to the Et-related disease detection method of the present invention, a living body-derived sample containing Et or having a possibility of containing Et is used as the "LAM-containing sample" of the Et-measuring method of the present invention.

The Et-related disease to be detected is not particularly limited, so long as it is a disease which is caused based on Et. Examples include endotoxemia and Gram-negative bacterial infection.

In addition, the "sample derived from the living body" is not particularly limited too, but a body fluid is preferable. The body fluid is not particularly limited, so long as it is a body fluid that contains Et or has a possibility of containing the same. Examples include blood (according to this specification, this is used as a general idea which includes serum and plasma too), urine, sweat, saliva, tears, synovial fluid, expectoration, milk, spinal fluid and the like. Among these, blood is preferable.

In this connection, when blood is used as the "sample derived from the living body", it is preferable to remove or inactivate *Limulus* reaction-interfering factors in blood (serine protease, serine protease inhibitor, etc.) in advance by a conventionally known method (e.g., the method described in JP-A-58-85162, etc.)

An Et-related disease can be detected in such a sample by using the Et-measuring method of the present invention.

As described above, the "detection" as used in this specification is a general idea which includes not only qualitative detection (detection of the presence or absence of an Et-related disease) but also quantitative measurement (detection of the malignancy of an Et-related disease, etc.).

An Et-related disease can be qualitatively measured by detecting the presence or absence of a *Limulus* reaction. Since Et induces the *Limulus* reaction, an Et-related disease is caused or there is a possibility of the Et-related disease when the *Limulus* reaction is detected.

As the quantitative measurement of an Et-related disease, various methods can be employed in response to the object. For example, strict determination can be carried out by preparing a calibration curve or a relational expression on the relationship between the Et concentration and the strength of *Limulus* reaction using a sample having already known Et concentration and using this. In addition, when strict determination is not necessary, amounts of Et between samples may be compared using two or more samples. Since Et induces a *Limulus* reaction, the amount of Et in a sample is large when the strength of the *Limulus* reaction is high, so that this can be correlated with a fact that malignancy of the Et-related disease is high or there is a possibility thereof.

<8> Et-Measuring Kit of the Present Invention

The Et-measuring kit of the present invention is a kit for measuring Et, which comprises a *Limulus* reagent and one or more substance(s) selected from the following group as components:

a surfactant, an anti-tuberculosis antibody, an anti-LAM antibody, BG, a carboxymethylated BG, a factor G activation inhibitor and a strong alkaline substance.

Explanations for the "*Limulus* reagent" and the above-described various substances are the same as in the above-described <1> and <5>. That is, it is preferable that this *Limulus* reagent to be used herein is also an Et-specific *Limulus* reagent.

The Et-measuring kit of the present invention may further contain another component, so long as it contains at least a "*Limulus* reagent" as a component. Examples of such a component include distilled water for blank test use, a reaction reagent solution, a buffer for reaction use and the like. In addition, the Et-measuring kit of the present invention can also contain a positive control (QC control) or the like for the purpose of keeping the practice level between measuring batches at a certain level.

These components can be preserved by containing in respectively separate containers.

Et using the Et-measuring kit of the present invention can be measured in accordance with the Et-measuring method of the present invention described in the above-described <6>.

<9> Et-Related Disease Detection Kit of the Present Invention

The Et-related disease detection kit of the present invention is a kit for detecting an Et-related disease, which comprises the Et-measuring kit of the present invention. Explanation for the Et-measuring kit of the present invention should be referred to the above-described <8>.

Explanation for the Et-related disease to be detected by the Et-related disease detection kit of the present invention and explanation of the "sample derived from the living body" and the like are the same as in the Et-related disease detection method of the present invention in the above-described <7>. That is, the Et-related disease to be detected includes endotoxemia and Gram-negative bacterial infection, and it is preferable that the "sample derived from the living body" is blood. In addition, it is also the same as in the above-described <7> that when blood is used as the "sample derived from the living body", it is preferable to remove or inactivate *Limulus* reaction-interfering factors in blood (serine protease, serine protease inhibitor, etc.) in advance.

An Et-related disease using the Et-related disease detection kit of the present invention can be detected in accordance with the Et-related disease detection method of the present invention described in the above-described <7>.

<10> BG-Measuring Method of the Present Invention

The BG-measuring method of the present invention is a method for measuring BG using a *Limulus* reagent in a "LAM-containing sample", which comprises at least a step of removing reactivity of LAM with a *Limulus* reagent by the reactivity-removing method of the present invention.

Explanations for the "*Limulus* reagent" and the "LAM-containing sample" are the same as in the LAM-measuring method of the present invention of the above-described <1>.

In addition, explanation for the reactivity-removing method of the present invention should be referred to the above-described <5>. However, it is necessary in this case to use a substance other than BG, a carboxymethylated BG and a factor G activation inhibitor.

The BG-measuring method of the present invention may contain other steps, so long as it is a method for measuring BG using a *Limulus* reagent wherein it comprises a step of removing reactivity of LAM with a *Limulus* reagent by the reactivity-removing method of the present invention.

In addition, explanations of the timing for applying the reactivity-removing method of the present invention and of the "contact" and the like are the same as in the Et-measuring method of the present invention of the above-described <6>.

According to the BG-measuring method of the present invention, the reactivity of LAM in the "LAM-containing sample" with a *Limulus* reagent is removed, so that BG in the sample can be measured without influence of LAM.

Explanation for the detection and measurement of the *Limulus* reaction induced by BG, explanation of the "measurement" and the like are also the same as in the Et-measuring method of the present invention of the above-described <6>.

<11> Mycosis Detection Method of the Present Invention

The mycosis detection method of the present invention is a method for detecting mycosis, which comprises using the BG-measuring method of the present invention.

In the mycosis detection method of the present invention, the BG-measuring method of the present invention is directly applied to the detection of mycosis.

Explanation for the BG-measuring method of the present invention should be referred to the above-described <10>. In the mycosis detection method of the present invention, a sample derived from the living body which contains BG or has a possibility of containing BG is used as the "LAM-containing sample" in the BG-measuring method of the present invention.

The mycosis to be detected is not particularly limited, so long as it is a disease which is classified into the category of mycosis. Examples include deep fungal infection and the like.

Explanation for the "sample derived from the living body" is the same as in the Et-related disease detection method of the present invention in the above-described <7>. It is also the same as the above-described <7> that when blood is used as the "sample derived from the living body", it is preferable to remove or inactivate *Limulus* reaction-interfering factors in blood (serine protease, a serine protease inhibitor, etc.) in advance by a conventionally known method (e.g., the method described in JP-A-58-85162, etc.).

Mycosis can be detected in such a sample by using the BG-measuring method of the present invention.

Explanation for the "detection" and the like are also the same as in the above-described <7>.

<12> BG-Measuring Kit of the Present Invention

The BG-measuring kit of the present invention is a kit for measuring BG, which comprises a *Limulus* reagent and one or more substance(s) selected from the following group as components:

a surfactant, an anti-tuberculosis antibody, an anti-LAM antibody, a strong alkaline substance, polymyxin B, colistin, concanavalin A, histidine and histamine.

Explanations for the "*Limulus* reagent" and the above-described various substances are the same as in the above-described <1> and <5>. However, it is preferable that the *Limulus* reagent to be used herein is a BG-specific *Limulus* reagent.

The BG-measuring kit of the present invention may further comprise other components, so long as it comprises at least the "*Limulus* reagent" as a component. Explanation for such components and the like are the same as in the Et-measuring kit of the present invention of the above-described <8>.

BG using the BG-measuring kit of the present invention can be measured in accordance with the BG-measuring method of the present invention of the above-described <10>.

<13> Mycosis Detection Kit of the Present Invention

The mycosis detection kit of the present invention is a kit for detecting mycosis, which comprises the BG-measuring kit of the present invention. Explanation for the BG-measuring kit of the present invention should be referred to the above-described <12>.

Explanation for the mycosis to be detected by the mycosis detection kit of the present invention, explanation of the "sample derived from the living body" to be used and the like are the same as in the mycosis detection method of the present invention of the above-described <11>. That is, the mycosis to be detected includes a deep fungal infection, and it is preferable that the "sample derived from the living body" to be used is blood. In addition, it is also the same as in the above-described <11> that when blood is used as the "sample derived from the living body", it is preferable to remove or inactivate *Limulus* reaction-interfering factors in blood (serine protease, a serine protease inhibitor, etc.) in advance.

Mycosis using the mycosis detection kit of the present invention can be detected in accordance with the mycosis detection method of the present invention of the above-described <11>.

<14> Agent for Binding of the Present Invention

The invention further provides an agent for binding of LAM, which comprises one or more substance(s) selected from the following group as an active ingredient (hereinafter referred to as "agent for binding of the present invention"):

an anti-tuberculosis antibody, an anti-LAM antibody, $(1\rightarrow3)$-$\beta$-glucan, a carboxymethylated $(1\rightarrow3)$-$\beta$-glucan, a factor G activation inhibitor, polymyxin B, colistin, concanavalin A, histidine and histamine.

Explanation for the above-described various substances is the same as in the above-described <5>.

In addition, the agent for binding of the present invention may contain another substance, so long as it contains at least one of the above-described substrate group as an active ingredient. The "another substance" as used herein is not particularly limited, so long as it does not substantially spoil the LAM-binding action of the substance as an active ingredient of the agent for binding of the present invention. Examples of such an "another substance" include those which do not substantially spoil the LAM-binding action of the active ingredient substance of the agent for binding of the present invention, among fillers, buffers, stabilizers, preservatives and the like which are used in the preparation of general medicines or reagents.

In this connection, the term "agent for binding of LAM" as used herein means an agent which is used for the purpose of binding the active ingredient substance in the preparation to LAM.

In addition, since the active ingredient substance binds to LAM, the agent for binding of the present invention can, for example, be used in the detection and measurement of LAM, removal of LAM and the like.

That is, LAM can be detected or measured by allowing the agent for binding of the present invention to contact with LAM (allowing a molecule of the active ingredient substance of the agent for binding of the present invention to contact with a LAM molecule), and then detecting the active ingredient substance bonded to LAM, directly or after its elution. In this case, the active ingredient substance in the agent for binding of the present invention may be labeled with a substance which can be detected as a certain specific signal (e.g., enzyme, radioisotope, fluorescence dye, chemiluminescence substance, hapten, metal particle, specific coupling pair, etc.). The labeling method and its detection and measuring methods are not particularly limited too, and conventionally known techniques can be used.

In addition, LAM in a solution can be removed by allowing the agent for binding of the present invention to adhere to an insoluble carrier (allowing a molecule of the active ingredient substance in the agent for binding of the present invention to form a solid phase on an insoluble carrier), binding LAM to the active ingredient substance molecule made into a solid phase by allowing this to contact with a solution containing LAM, and then separating the carrier to which the active ingredient substance has been adhered, from the solution. The carrier to which the active ingredient substance in the agent for binding of the present invention is adhered and the adhering method are not particularly limited, and conventionally known techniques can be used.

Accordingly, the present invention also includes general ideas such as a method for detecting or measuring LAM, which comprises using one or more substance(s) selected from the following group, a kit for measuring LAM, which comprises one or more substance(s) selected from the following group as a component(s), a method for removing LAM, which comprises using a carrier to which one or more substance(s) selected from the following group are adhered, and an agent for removing LAM (adsorption removal agent), which comprises a carrier to which one or more substance(s) selected from the following group are adhered:

an anti-tuberculosis antibody, an anti-LAM antibody, $(1\rightarrow3)$-$\beta$-glucan, a carboxymethylated $(1\rightarrow3)$-$\beta$-glucan, a factor G activation inhibitor, polymyxin B, colistin, concanavalin A, histidine and histamine.

<15> Examples of the Illustrative Embodiments of the Present Invention

For example, all of specific embodiments shown below are included in the present invention. In this connection, the following embodiments are simple illustrations, and technical scope of the present invention is not restricted thereby.

(1) A method for measuring Et activity (concentration) in a LAM-containing sample without influence of the coexisting LAM, wherein the sample is allowed in advance to contact with at least one substance selected from a surfactant, pachyman, an antituberculous dead cell antibody and an anti-LAM antibody, and then measured using an Et-specific *Limulus* reagent.

(2) A method for measuring LAM activity (concentration) in a LAM-containing sample without influence of the coexisting Et, wherein the sample is heated in advance, and then measured using an Et-specific *Limulus* reagent.

(3) A method for detecting endotoxemia or Gram-negative bacterial infection by measuring Et concentration in blood by the method of the above-described (1).

(4) A method for detecting tubercle bacillus infection by measuring LAM concentration in blood by the method of the above-described (2).

(5) A method for measuring Et activity (concentration) in a LAM-containing sample without influences of the coexisting LAM and BG, wherein the sample is allowed in advance to contact with a surfactant and a factor G activation inhibitor, and then measured using a *Limulus* reagent which reacts with both of Et and BG.

(6) A method for measuring Et activity (concentration) in a LAM-containing sample without influences of the coexisting LAM and BG, wherein the sample is allowed in advance to contact with pachyman and a factor G activation inhibitor, and then measured using a *Limulus* reagent which reacts with both of Et and BG.

(7) A method for measuring Et activity (concentration) in a LAM-containing sample without influences of the coexisting LAM and BG, wherein the sample is allowed in advance to contact with an antituberculous dead cell antibody and a factor G activation inhibitor, and then measured using a *Limulus* reagent which reacts with both of Et and BG.

(8) A method for measuring Et activity (concentration) in a LAM-containing sample without influences of the coexisting LAM and BG, wherein the sample is allowed in advance to contact with an anti-LAM antibody and a factor G activation inhibitor, and then measured using a *Limulus* reagent which reacts with both of Et and BG.

(9) A method for measuring Et activity (concentration) in a LAM-containing sample without influences of the coexisting LAM and BG, wherein the sample is allowed in advance to contact with a surfactant and curdlan (and/or carboxymethylcurdlan), and then measured using a *Limulus* reagent which reacts with both of Et and BG.

(10) A method for measuring Et activity (concentration) in a LAM-containing sample without influences of the coexisting LAM and BG, wherein the sample is allowed in advance to contact with pachyman and curdlan (and/or carboxymethylcurdlan), and then measured using a *Limulus* reagent which reacts with both of Et and BG.

(11) A method for measuring Et activity (concentration) in a LAM-containing sample without influences of the coexisting LAM and BG, wherein the sample is allowed in advance to contact with an antituberculous dead cell antibody and curdlan (and/or carboxymethylcurdlan), and then measured using a *Limulus* reagent which reacts with both of Et and BG.

(12) A method for measuring Et activity (concentration) in a LAM-containing sample without influences of the coexisting LAM and BG, wherein the sample is allowed in advance to contact with an anti-LAM antibody and curdlan (and/or carboxymethylcurdlan), and then measured using a *Limulus* reagent which reacts with both of Et and BG.

(13) A method for measuring Et activity (concentration) in a LAM-containing sample without influences of the coexisting LAM and BG, wherein the sample is heated in advance in the presence of a factor G activation inhibitor, and then measured using a *Limulus* reagent which reacts with both of Et and BG.

(14) A method for measuring LAM activity (concentration) in a LAM-containing sample without influences of the coexisting Et and BG, wherein the sample is heated in advance in the presence of curdlan and/or carboxymethylcurdlan, and then measured using a *Limulus* reagent which reacts with both of Et and BG.

(15) A method for detecting tuberculous infection by measuring LAM activity (concentration) in blood, using plasma or serum as the "LAM-containing sample" in the above-described (13) and (14).

(16) A method for measuring Et activity (concentration) in blood without influences of the coexisting LAM and BG and thereby detecting endotoxemia or Gram-negative bacterial infection, wherein plasma or serum is diluted in advance with a surfactant and aqueous solutions containing "at least one substance selected from pachyman, an antituberculous dead cell antibody and an anti-LAM antibody" and "at least one substance selected from an factor G activation inhibitor, curdlan and carboxymethylcurdlan", heated and then measured using a *Limulus* reagent which reacts with both of Et and BG.

(17) A method for measuring Et activity (concentration) in blood without influences of the coexisting LAM and BG and thereby detecting endotoxemia or Gram-negative bacterial infection, wherein plasma or serum is diluted in advance with a surfactant and an aqueous solution containing "at least one substance selected from pachyman, an antituberculous dead cell antibody and an anti-LAM antibody", heated and then measured using an Et-specific *Limulus* reagent.

(18) A method for detecting a deep fungal infection, wherein BG activity (concentration) in blood is measured without influences of the coexisting LAM and Et, by heating plasma or serum in advance in the presence of polymyxin B and then measuring it using a *Limulus* reagent which reacts with both of Et and BG.

(19) A method for detecting or measuring LAM, by allowing a molecule of the active ingredient substance (labeled) of the agent for binding of the present invention to contact with a LAM molecule, and then detecting the substance (the label) bonded to LAM directly or after elution.

(20) A method for removing LAM in a solution, by making a solid phase of a molecule of the active ingredient substance of the agent for binding of the present invention onto an insoluble carrier, allowing this to contact with a solution containing LAM, and then removing the carrier by separating from the solution.

Examples of the present invention are specifically described below. However, the technical scope of the present invention is not limited thereto.

In this connection, the LAM used in the examples is an LAM (available from Nacalai Tesque) isolated and purified to a high purity from dead cells of a strain of a human type tubercle bacillus (Aoyama B strain; *Mycobacterium tuberculosis* Aoyama-B) by organic solvent extraction and column chromatography.

EXAMPLE 1

This LAM was dissolved in distilled water (Et- and BG-free) to a concentration of 200 ng/ml to prepare a LAM-containing sample. This sample was subjected to each of the following various treatments, and then 25 μl of the sample was mixed with 100 μl of an Et-specific *Limulus* reagent (trade name: Endospec ES Test MK, available from SEIKAGAKU CORPORATION) in an Et- and BG-free microtiter plate (Toxipet Plate 96F, available from SEIKAGAKU CORPORATION), and measured at 37° C. for 30 minutes in a microplate reader (Wellreader SK 603, available from SEIKAGAKU CORPORATION).

Thereafter, the degree of the *Limulus* reaction was calculated from the ratio of change (mAbs/min) of absorbance [A405 nm-492 nm (control wavelength)] per minute and compared with that of an untreated sample (control).

In this connection, the *Limulus* reagent used herein had been treated in such a manner that factor C alone can be activated by removing the reactivity of factor G (treated such that it reacts only with Et). Accordingly, when the *Limulus* reaction was detected, it means that the factor C was activated (that the added sample has the ability to activate factor C).

Treatments:

Polymyxin B Treatment:

The same amount of polymyxin B sulfate (Sigma) was added to a LAM-containing sample to a final concentration of 1 mg/ml and mixed.

Acid Heating Treatment:

The same amount of HCl aqueous solution was added to a LAM-containing sample to a final concentration of 0.2 M, mixed and incubated at 37° C. for 60 minutes.

Alkali Heating Treatment:

The same amount of KOH aqueous solution was added to a LAM-containing sample to a final concentration of 0.2 M, mixed and incubated at 37° C. for 60 minutes.

Boiling Treatment:

A LAM-containing sample was boiled for 60 minutes.

Surfactant Treatment:

The same amount of each of various nonionic surfactants (Brij 56, Triton-N-101, Triton X-405, Triton X-114 and Tergitol NP-9) was added to a LAM-containing sample to a final concentration of from 0.005 to 0.5% and mixed.

BG Treatment:

The same amount of pachyman was added to a LAM-containing sample to a final concentration of 50 pg/ml and mixed.

Concanavalin A Treatment:

To 0.25 g in wet weight of Concanavalin A (Con A) Sepharose 4B (available from Amersham Bioscience), 1 ml of an LAM aqueous solution was added, mixed and then centrifuged at 3,000 rpm for 10 minutes, and the thus obtained supernatant was used.

Reactivity with an Anti-Tuberculosis Antibody:

Reactivity of LAM with an anti-tuberculosis antibody (an anti-human type tubercle bacillus dead cell monoclonal antibody) was examined.

Anti-Factor C Antibody Treatment:

A "solution prepared by adding 140 µl of 20 times-diluent of a mouse anti-factor C monoclonal antibody (2C12; ascites) to 1 vial of an Et-specific *Limulus* reagent (trade name: Endospec ES Test MK, available from SEIKAGAKU CORPORATION)" was added to a LAM-containing sample and a *Limulus* reaction was carried out.

The results are shown in Table 1. In this connection, the "+" in Table 1 shows that the reaction was detected, and the illustrative numerical values in Table 1 mean relative values when the reactivity in the untreated sample (control) was defined as 100%.

TABLE 1

| Untreated sample (control) | + |
| --- | --- |
| Polymyxin B treatment | 7.5% |
| Acid heating treatment | 72.0% |
| Alkali heating treatment | 0% |
| Boiling treatment | 44.4% |
| Surfactant treatment | 0% |
| BG treatment | 1.6% |
| Concanavalin A treatment | 5.7% |
| Reactivity with anti-tuberculosis antibody | + |
| Anti-factor C antibody treatment | 0% |

Based on this result, it was found that LAM has the reactivity with a *Limulus* reagent (has the ability to activate the factor C). Accordingly, it was shown that measurement of LAM and detection of acid-fast bacteria keeping LAM as a cell wall component are possible by using the *Limulus* reagent.

Also, it was found that the *Limulus* reagent reactivity owned by LAM can be removed or reduced by using polymyxin B, a strong alkaline substance, various nonionic surfactant, BG, concanavalin A and the like.

Also, since it was confirmed that LAM reacts with an anti-tuberculosis antibody, it was suggested that the reactivity of LAM with a *Limulus* reagent can also be removed or reduced by allowing a LAM-containing sample with the anti-tuberculosis antibody in advance.

In addition, since it was shown that LAM binds to an anti-tuberculosis antibody, concanavalin A and the like, it was indicated that removal of LAM and the like can also be carried out using them.

Accordingly, it was shown that Et and BG can be measured out without influence of LAM, by treating a LAM-containing sample with such substances. In addition, it was shown that Et-related diseases and mycosis can also be detected by this without influence of LAM. Further, it was shown also that an anti-tuberculosis antibody, concanavalin A and the like can be used as agents for binding of LAM and can be used for the removal of LAM and the like.

EXAMPLE 2

(1) Production Example of the LAM-Measuring Kit of the Present Invention (Acid-Fast Bacteria Detection Kit of the Present Invention)

A kit containing the following reagents was prepared.

A. Et-Specific Chromogenic *Limulus* Reagent

A freeze-dried product comprising a lysate prepared from blood cell (amoebocyte) of a horseshoe crab (*Tachypleus tridentatus*) in accordance with the method described in Reference Example 3 of WO 90/02951, from which the reactivity of factor G was removed, a coloring synthetic substrate (Boc-Leu-Gly-Arg-pNA) and the like.

B. Distilled Water (Et-Free)

This is used in the blank test, for the dissolution and dilution of positive control, dilution of test samples and the like.

C. Buffer 0.2 mol/l Tris-HCl buffer (pH 8.0). This is used for the dissolution of the *Limulus* reagent and in the reaction.

D. Positive Control

A freeze-dried product containing LAM.

LAM (an acid-fast bacterium) in a test sample can be measured and detected without influence of Et, by heating the test sample in advance by the method described in the above-described "<1> LAM-measuring method of the present invention" and then carrying out the *Limulus* reaction using this kit.

(2) Production Example of the Et-Measuring Kit of the Present Invention (Et-Related Disease Detection Kit of the Present Invention)

A kit containing the following reagents was prepared.

A. Et-Specific Chromogenic *Limulus* Reagent

Endospec ES Test MK (trade name; available from SEIKAGAKU CORPORATION) is used.

B. Distilled Water (Et-Free)

This is used in the blank test, for the dissolution and dilution of positive control, dilution of test samples and the like.

C. Buffer 0.2 mol/l Tris-HCl buffer (pH 8.0). This is used for the dissolution of the *Limulus* reagent and in the reaction.

D. Positive Control

A freeze-dried product containing Et derived from an *Escherichia coli* 0111:B4.

E. Blood Pre-Treating Solution

First solution: 0.2 mol/l KOH, 0.2% polybrene
Second solution: 0.2% Triton X-100, 0.14% ethyleneimine polymer, 0.02 mol/l $CaCl_2$, 0.06 mol/l Bicine This pre-treating solution is used when plasma or serum is used as a test sample, in order to inactivate *Limulus* reaction-interfering factors contained therein.

The first solution is mixed with the second solution immediately before use.

F. Surfactant

An aqueous solution containing 0.01% Tergitol NP-9.

The surfactant is used for removing the *Limulus* reagent reactivity of LAM. That is, Et (Et-related disease) can be measured and detected without influence of LAM, by treating a test sample (treated with the blood pre-treating solution in the case of a blood sample) in advance with this surfactant and then carrying out the *Limulus* reaction.

While the invention has been described in detail and with reference to specific embodiments thereof, it will be apparent to one skill in the art that various changes and modifications can be made therein without departing from the spirit and scope thereof.

This application is based on Japanese patent application No. 2003-425472 filed on Dec. 22, 2003, the entire contents of which are incorporated hereinto by reference. All references cited herein are incorporated in their entirety.

Industrial Applicability

The LAM-measuring method of the present invention, the acid-fast bacterium detection method of the present invention, the LAM-measuring kit of the present invention and the acid-fast bacterium detection kit of the present invention can be applied to the measurement and detection of LAM and acid-fast bacteria.

In addition, the reactivity-removing method of the present invention can be applied to the removal of influence of LAM in the *Limulus* reaction.

Also, the Et-measuring method of the present invention, the Et-related disease detection method of the present invention, the Et-measuring kit of the present invention and the Et-related disease detection kit of the present invention can be applied to the measurement and detection of Et and Et-related diseases.

Also, the BG-measuring method of the present invention, the mycosis detection method of the present invention, the BG-measuring kit of the present invention and the mycosis detection kit of the present invention can be applied to the measurement and detection of BG and mycosis.

In addition, the agent for binding of the present invention can be used in the detection and measurement of LAM, the kit to be used therein, the removal method of LAM, the LAM-removing agent (an adsorption removal agent) and the like.

The invention claimed is:

1. A method to detect lipoarabinomannan (LAM) in a LAM-containing sample without influence of the coexisting endotoxin (Et), wherein the sample is heated in advance, and then detected using an Et-specific *Limulus* reagent comprising:

heating the lipoarabinomannan-containing sample in a temperature range of 37° C. to 121° C.;

keeping the heated state for 5 to 60 minutes before contact with an endotoxin-specific *Limulus* reagent;

contacting the heated sample containing lipoarabinomannan with an endotoxin-specific *Limulus* reagent;

wherein the LAM in said sample activates factor C in the *Limulus* reagent, thereby inducing a *Limulus* reaction; and detecting the *limulus* reaction to detect the LAM in the sample.

* * * * *